United States Patent
Fumex et al.

(10) Patent No.: US 10,653,444 B2
(45) Date of Patent: May 19, 2020

(54) PERFORATING TROCAR

(71) Applicant: Merit Medical Systems, Inc., South Jordan, UT (US)

(72) Inventors: Laurent Fumex, Madison, CT (US); Thierry Masseglia, La Garde (FR)

(73) Assignee: Merit Medical Systems, Inc., South Jordan, UT (US)

( * ) Notice: Subject to any disclaimer, the term of this patent is extended or adjusted under 35 U.S.C. 154(b) by 8 days.

(21) Appl. No.: 14/434,157

(22) PCT Filed: Jun. 5, 2014

(86) PCT No.: PCT/FR2014/051346
§ 371 (c)(1),
(2) Date: Apr. 8, 2015

(87) PCT Pub. No.: WO2015/001211
PCT Pub. Date: Jan. 8, 2015

(65) Prior Publication Data
US 2016/0367287 A1 Dec. 22, 2016

(30) Foreign Application Priority Data

Jul. 1, 2013 (FR) ..................................... 13 56391

(51) Int. Cl.
*A61B 17/34* (2006.01)
*A61B 10/02* (2006.01)

(52) U.S. Cl.
CPC ........ *A61B 17/3417* (2013.01); *A61B 10/025* (2013.01); *A61B 17/3472* (2013.01); *A61B 17/3476* (2013.01); *A61B 2010/0258* (2013.01); *A61B 2017/3454* (2013.01)

(58) Field of Classification Search
CPC .......................... A61B 10/025; A61B 17/3417
See application file for complete search history.

(56) References Cited

U.S. PATENT DOCUMENTS

| 5,389,077 A | * | 2/1995 | Melinyshyn | ....... A61B 17/3417 604/117 |
| 5,624,459 A | * | 4/1997 | Kortenbach | ....... A61B 17/3417 604/164.01 |
| 6,575,919 B1 | | 6/2003 | Reiley et al. | |

(Continued)

FOREIGN PATENT DOCUMENTS

| DE | 3542948 | 6/2018 |
| WO | 2006061514 | 6/2006 |

OTHER PUBLICATIONS

Search Report dated 2013.
European Search Report dated May 24, 2018 for EP17204286.3.

*Primary Examiner* — Patrick Fernandes
(74) *Attorney, Agent, or Firm* — Stoel Rives LLP

(57) ABSTRACT

The invention relates to a device in the form of a perforating trocar and is intended in particular to be used for surgery and interventional radiology. The device comprises an outer sleeve (5) having a rigid tube (8), and a mandrel (6) having a rod (18). The rod (18) is suitable for sliding in the outer sleeve (5) and has, at its distal end, a perforating tip (21, 33). The rod (18) additionally has a longitudinal groove (20) arranged on the surface of the rod (18), and extending from the distal end to the proximal end of the rod (18), in order to allow the device to slide on a guide pin.

8 Claims, 5 Drawing Sheets

(56) References Cited

U.S. PATENT DOCUMENTS

| | | | |
|---|---|---|---|
| 7,850,620 B2 | 12/2010 | Miller et al. | |
| 2003/0212343 A1* | 11/2003 | Plishka | A61B 10/0275 600/564 |
| 2003/0225344 A1 | 12/2003 | Miller | |
| 2003/0225411 A1* | 12/2003 | Miller | A61B 10/025 606/80 |
| 2008/0045860 A1 | 2/2008 | Miller et al. | |
| 2008/0243163 A1* | 10/2008 | Masseglia | A61B 10/025 606/185 |
| 2009/0048575 A1 | 2/2009 | Waters | |
| 2009/0204024 A1* | 8/2009 | Miller | A61B 10/025 600/567 |

* cited by examiner

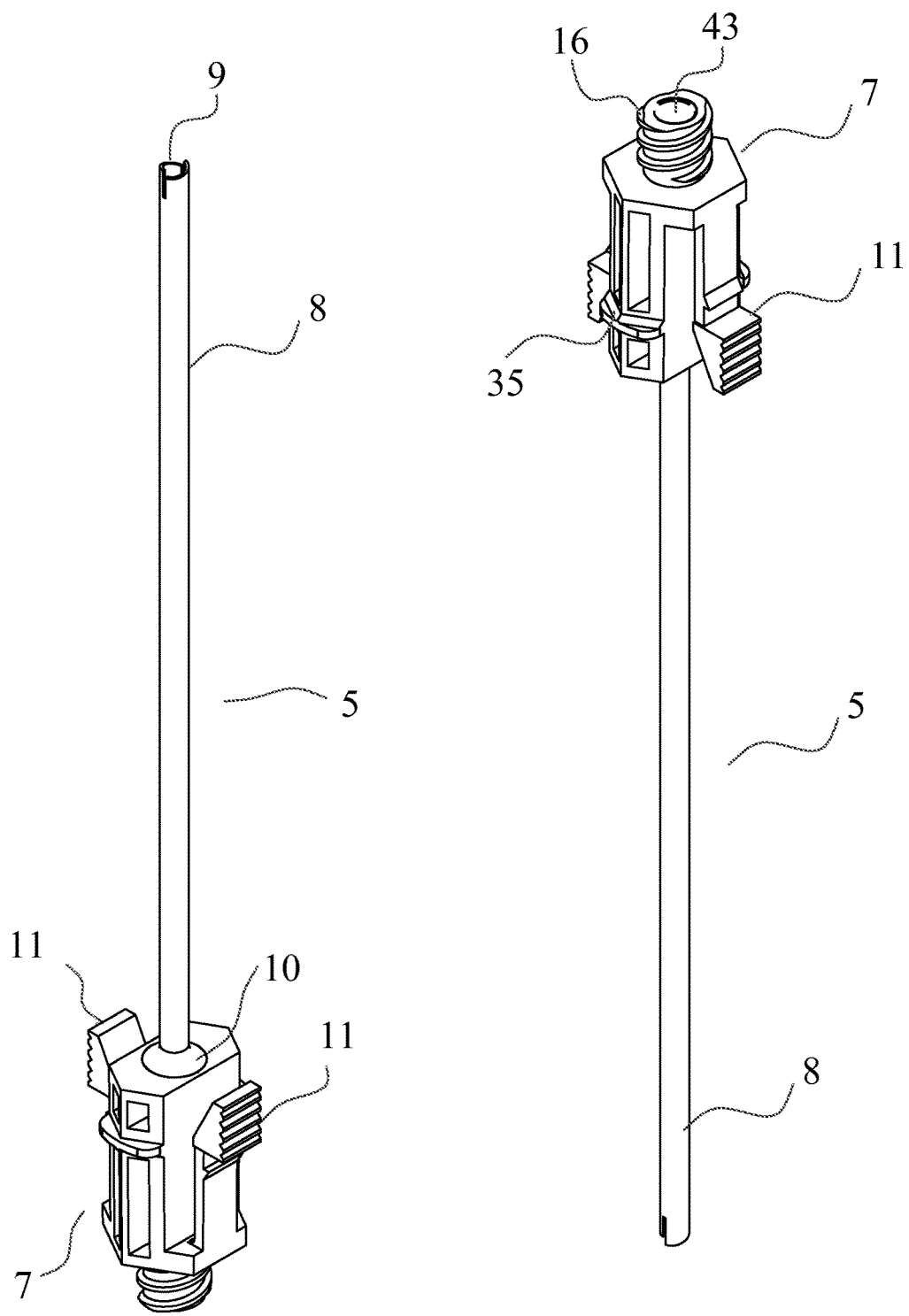

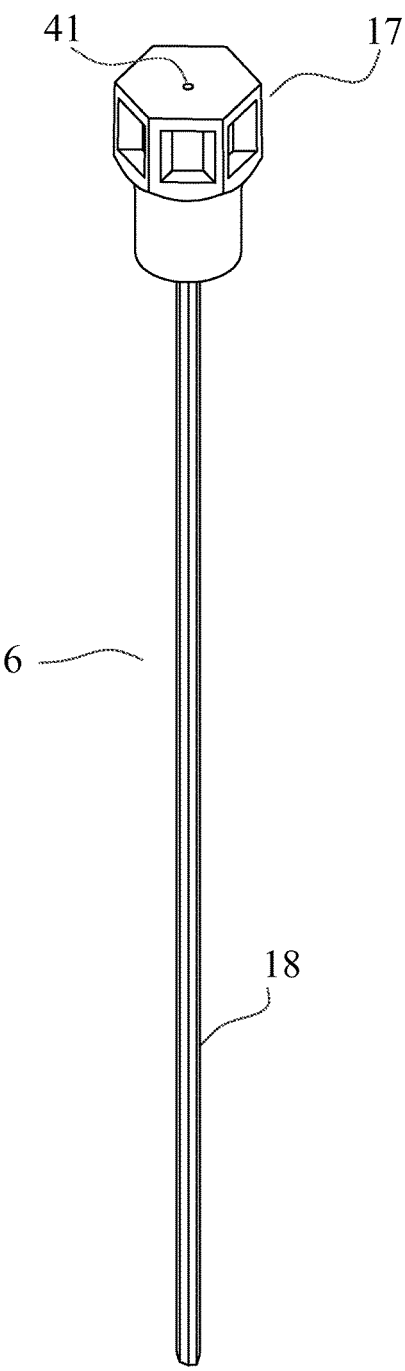
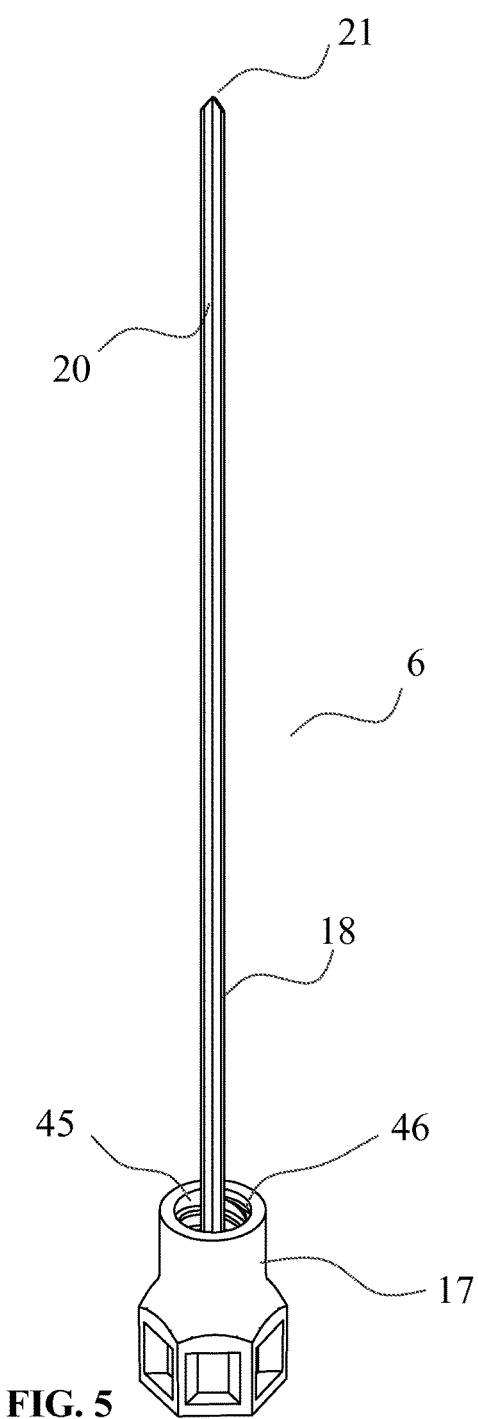
FIG. 4
FIG. 5

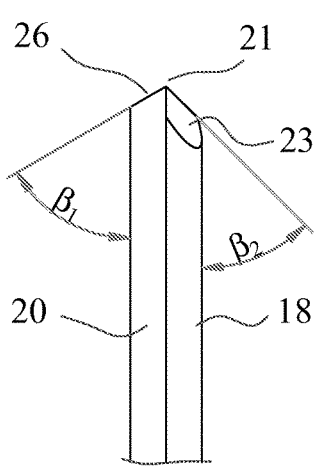 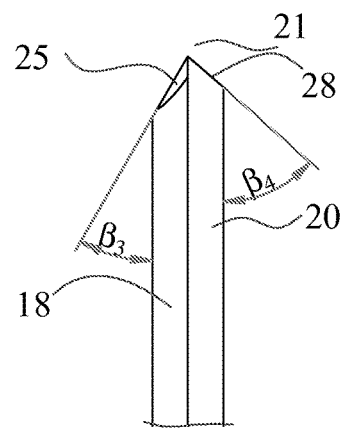 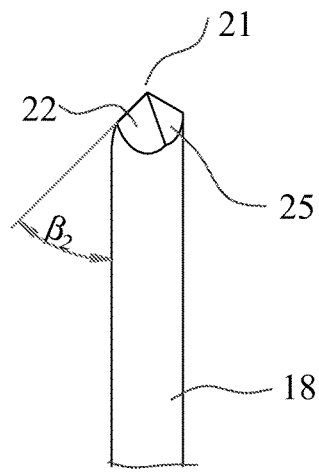
FIG. 6  FIG. 7  FIG. 8
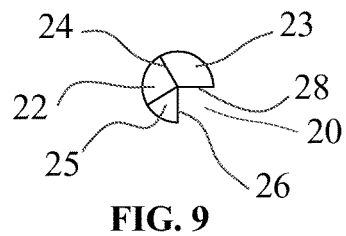
FIG. 9
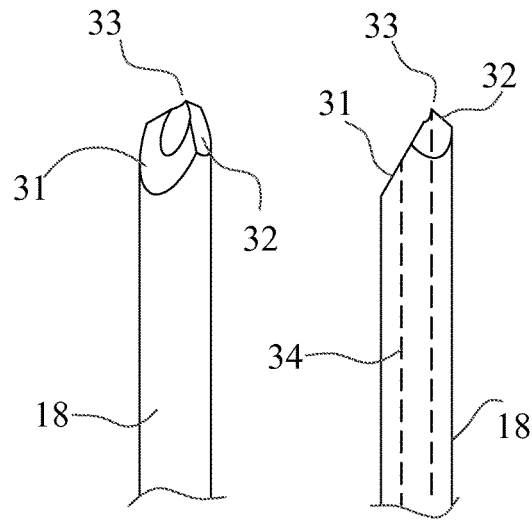
FIG. 10  FIG. 11

PERFORATING TROCAR

RELATED APPLICATIONS

This application is a National Phase Application of PCT/FR2014/051346, filed on Jun. 5, 2014, which in turn claims the benefit of priority from French Patent Application No. 13 56391 filed on Jul. 1, 2013, the entirety of which are incorporated herein by reference.

BACKGROUND

Field of the Invention

The present invention relates to a device that can be used in surgery and in interventional radiology, and more particularly to a perforating trocar that can be used especially in the field of percutaneous procedures for bone or marrow biopsy, vertebroplasty, cementoplasty of the skeletal areas, and more generally the treatment of bone damage.

Description of Related Art

Various types of perforating trocars are known, which are surgical instruments used to drill bone in order to reach a zone where a bone biopsy is to be performed. These trocars are composed of a hollow outer tube, of which the end is more or less sharp, and of a rod, of which the end is ground in order to perforate the bone and which slides in the tube.

Thus, the patent application WO 2006/061514 describes a trocar intended for bone biopsy and comprising an outer tube, of which the distal end is divided into two segments with a helical cutting edge, in which a ground rod slides. This type of instrument is used manually by way of a handle.

The U.S. Pat. No. 7,850,620 describes a trocar intended for bone marrow biopsy and composed of an outer tube, of which the distal end has a traditional grinding for this type of instrument, combined with a ground rod. This instrument is used by coupling it to a drill.

The patent applications US 2003/225411 A1 and US 2009/0204024 A1 concern trocars intended for bone marrow biopsy. These trocars each have a rod with a notch permitting the removal of pieces of bone and of tissue. The U.S. Pat. No. 6,575,919 B1 describes a trocar with an inner opening permitting the passage of a needle.

The known perforating trocars are able to drill bone but cannot be guided on a pin at the same time. This shortcoming has two major disadvantages: the lack of precision at the moment of reaching the bone, and the risk of accidents. Percutaneous procedures are mainly performed with imaging and therefore based on images. The point of entry and the trajectory can thus be visualized and defined in advance. The importance of the precision of the point of entry is self-evident in the case of small bone lesions, since these have diameters of sometimes less than a millimetre; matters are of course more difficult when targeting a lesion located within a deep bone. Therefore, in obese patients, it is not uncommon to have to pass through 150 mm to 200 mm of soft tissue before reaching the cortical bone. Under such conditions, it is particularly difficult to keep the trajectory of the trocar, of which the diameter is approximately 2 mm, to within a millimetre. Moreover, there are risks associated with direction introduction of a perforating trocar when this bone is situated in a dense zone comprising organs, veins and nerves. Confronted by such situations, the practitioner will accept the need to perform more manoeuvres and will first of all manually insert a thin and minimally invasive rigid pin, which will serve as a guide for the various coaxial trocars and instruments in the course of the surgical procedure.

Perforated drill-bits are also known which are used in orthopaedics and which can drill the bone while being guided on a pin. However, these drill-bits are not used, or not often used, in a percutaneous procedure, even less so when the latter is performed manually. The use of these drill-bits requires that a pin first be inserted into the bone by means of a drill. This is because these drill-bits do not have a distal tip, since they are perforated all the way through so as to slide on the pin. Therefore, in the absence of an inserted pin, they risk sliding on the bone and deviating from the point of entry defined by the practitioner.

OBJECTS AND SUMMARY

The present invention relates to a device, in particular for surgery and interventional radiology, which efficiently provides good perforation while at the same time being entirely suitable to be guided on a rigid pin until contact with the bone. The invention also relates to a device with which the practitioner can choose to commence a surgical procedure manually and complete it using an automatic rotational drive means, such as a drill, if the hardness of the bone so demands, and this without losing the point of entry to the bone.

The device according to the present invention, in the form of a perforating trocar, comprises an outer sleeve having a rigid tube, and a mandrel having a rod. The rod is suitable for sliding in the outer sleeve and has, at its distal end, a perforating tip. The rod additionally has a longitudinal groove arranged on the surface of the rod, and extending from the distal end to the proximal end of the rod, in order to allow the device to slide on a guide pin.

According to an embodiment of the invention, the groove is V-shaped.

Preferably, the perforating tip is formed by bevelled grinding or sharpening of the distal end of the rod. According to a preferred variant, the distal end of the rod comprises three bevels, of which one is less inclined than the two others with respect to the axis of the rod, and a perforating tip centred with respect to the axis of the rod.

Advantageously, the distal end of the rod comprises at least one cutting ridge extending from the perforating tip to the edges of the rod. According to one embodiment, this cutting ridge is situated on one of the faces of the groove. Preferably, this cutting ridge is more inclined than another cutting ridge with respect to the axis of the rod.

The bevelled pyramidal grinding, with the cutting ridge whose angle is greatest with respect to the axis of the rod situated on one of the faces of the longitudinal groove, permits better penetration into the bone. Indeed, tests carried out on the bone marrow of cattle have shown that the tip thus formed penetrates up to 5 times more deeply than a traditional triangular tip.

According to a feature of the invention, the distal end of the tube comprises at least two segments with a helically shaped cutting edge.

Advantageously, the outer sleeve additionally comprises a connector piece at the proximal end of the tube, and the mandrel additionally comprises a stopper at the proximal end of the rod. The stopper is suitable for receiving the connector piece in order to form an integral assembly. The connector piece is perforated in order to permit the sliding of the rod, and the stopper is perforated in order to permit the sliding of the guide pin.

According to some embodiments, the assembly formed by the outer sleeve and the mandrel is mounted in a handle or in an automatic rotational drive means. For example, the automatic rotational drive means can be a drill having an endpiece in which the assembly is mounted.

Advantageously, the automatic drive means can be provided with a protective envelope. The protective envelope can, for example, be attached to the endpiece of a drill by means of a connector piece which is at the same time adapted to receive the outer sleeve of the perforating trocar.

For example, in the case of a bone lesion located in a dense cortical area, the practitioner, after providing local anaesthesia by conventional techniques, introduces the guide pin parallel to or through the anaesthetic needle in place until contact is made with the bone. The anaesthetic needle is then removed while leaving the guide pin in place. The device according to the invention, equipped with a removable handle, is introduced through the tissues, until in contact with the bone, by being guided on the pin. The pin is removed once the surface of the cortical bone is reached, then the practitioner drills the bone by turning the trocar manually, without losing the point of entry. In 80% to 90% of cases, the drilling will be performed manually, but if the wall of the bone is very hard, the practitioner may remove the removable handle and connect the trocar to a drill in order to complete the surgical procedure.

The simplicity of the structure of the device according to the invention means that, depending on the depth or location of the lesion, the user can be provided with a single instrument which permits a choice between a direct route and one guided on the pin, and of which the drilling can be manual or done using the drill, or else can be commenced manually and completed using the drill. The combination of drilling by hand and drilling with a drill permits a high level of precision of the surgical manoeuvre and also considerable power regardless of the hardness of the bone.

BRIEF DESCRIPTION OF THE DRAWINGS

Other features and advantages of the present invention will become clear from the following description of a preferred embodiment and by reference to the attached drawings, in which:

FIGS. 2 to 3 show perspective views of a tube of the device according to the invention mounted in a connector piece, forming an outer sleeve;

FIGS. 4 to 5 show perspective views of a grooved rod of the device according to the invention mounted in a stopper, forming a mandrel;

FIGS. 6 to 9 show views of an example of the distal end of the grooved rod;

FIGS. 10 and 11 show views of an example of the distal end of the rod provided with a hole;

DETAILED DESCRIPTION

Figure 1:
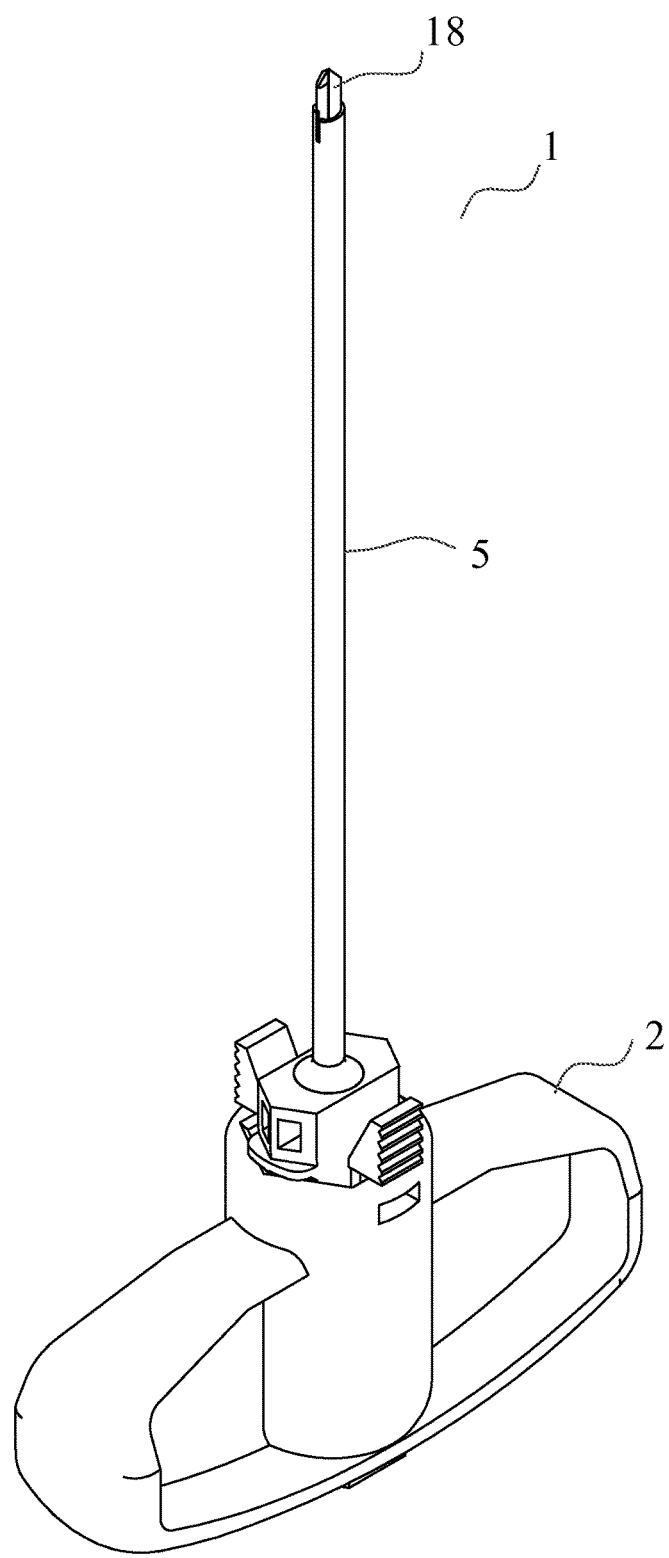
FIG. 1 shows a perspective view of a device according to the invention mounted in a handle.

The trocar 1, shown in FIG. 1, is composed of an outer sleeve 5, in which is mounted a mandrel (of which only the distal end of the rod 18 is visible in FIG. 1), and of a handle 2, in which the sleeve/mandrel assembly is inserted.

The outer sleeve 5, shown in FIGS. 2 and 3, has a connector piece 7 in which the bevelled tube 8 is accommodated. The tube 8 has a distal end 9 divided into two segments with a helical cutting edge as described in the application WO 2006/061514. The connector piece 7 has a hexagonal shape cooperating with hexagonal cavities 12 of the handle 2 and hexagonal cavities 13 of the endpiece 3 of a drill 4 (see also FIGS. 12 and 13). The connector piece 7 has a bore 10, in which the tube 8 is accommodated, and two flexible parts 11 that latch into recesses 14 of the handle 2 or into recesses 15 of the endpiece 3 of the drill 4.

The mandrel 6, shown in FIGS. 4 et 5, comprises a grooved rod 18 accommodated in a stopper 17. The grooved rod 18 has a V-shaped longitudinal groove 20 and a distal end of pyramidal shape. The stopper 17 has a hexagonal shape cooperating with the hexagonal cavities 12 of the handle 2 and the hexagonal cavities 13 of the endpiece 3 of the drill 4. The stopper 17 has a bore 45 in which the grooved rod 18 is accommodated, and a bore 41 permitting the passage of the guide pin.

The connector piece 7 of the outer sleeve 5 is completely perforated 43 in such a way as to permit the sliding of the rod 18. The end 16 of the outer sleeve 5 is in the form of a Luer connector permitting the screwing of the stopper 17. The stopper 17 has a thread 46 cooperating with the thread 16 of the connector piece 7, allowing it to be screwed in order to assemble the outer sleeve 5 and the mandrel 6.

FIGS. 6 to 9 shows views of an example of the distal end of the rod 18. The distal end of the rod 18 comprises a tip 21 having a pyramidal grinding with three bevels. Two of the bevels 22, 23 have the same inclination ($\beta_3$), preferably $\beta_3=30°$, with respect to the axis of the rod 18 and extend through approximately 120° of the cross section of the rod 18, generating a cutting ridge 24. The third bevel 25, inclined preferably by $\beta_1$ and at 40° with respect to the axis of the rod 18, generates a second cutting ridge 26. The second cutting ridge 26 is situated on one of the faces of the groove 20 and has an inclination $\beta_1$ greater than the inclination $\beta_2$ of the ridge 24 with respect to the axis of the rod 18. This permits better cutting of the bone since the second cutting ridge 26 has a greater angle of attack, generated by one of the faces of the groove 20. The inclination $\beta_1$ of the cutting ridge 26 is greater than the inclination $\beta_2$ of the cutting ridge 24 and than the inclination $\beta_4$ of the other cutting ridge 28 situated on the other face of the longitudinal groove. The intersection of the three bevels generates the tip 21 allowing the mandrel 6 not to slide on the bone.

The views in FIGS. 10 and 11 show a distal end of the rod 18 according to a variant. The rod 18 has, centred on its axis, a hole 34 allowing it to be guided on a pin. The distal end of the rod 18 has a pyramidal grinding with three bevels of the same inclination, of which one bevel 31 is greater than the other two bevels 32, in such a way as to generate a tip 33 situated on the edge of the hole 34.

Figure 12:
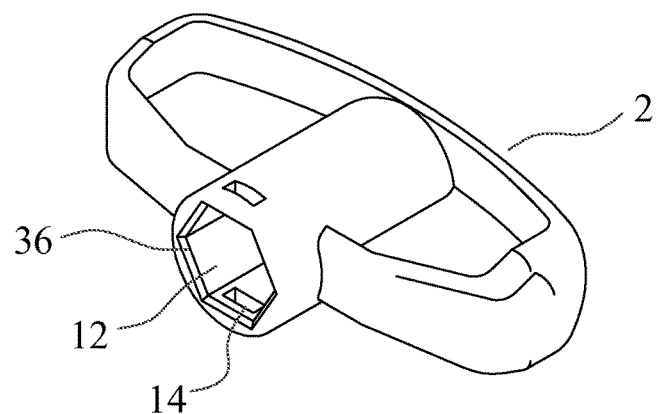
FIG. 12 shows a perspective view of a handle for receiving the assembly formed by the sleeve and the mandrel of the device according to the invention.

The perspective view in FIG. 12 shows the handle 2 with a hexagonal cavity 12 in which is mounted the outer sleeve 5 equipped with the mandrel 6. The flexible parts 11 of the connector piece 7 latch into the recesses 14 provided for this purpose.

Figure 13:
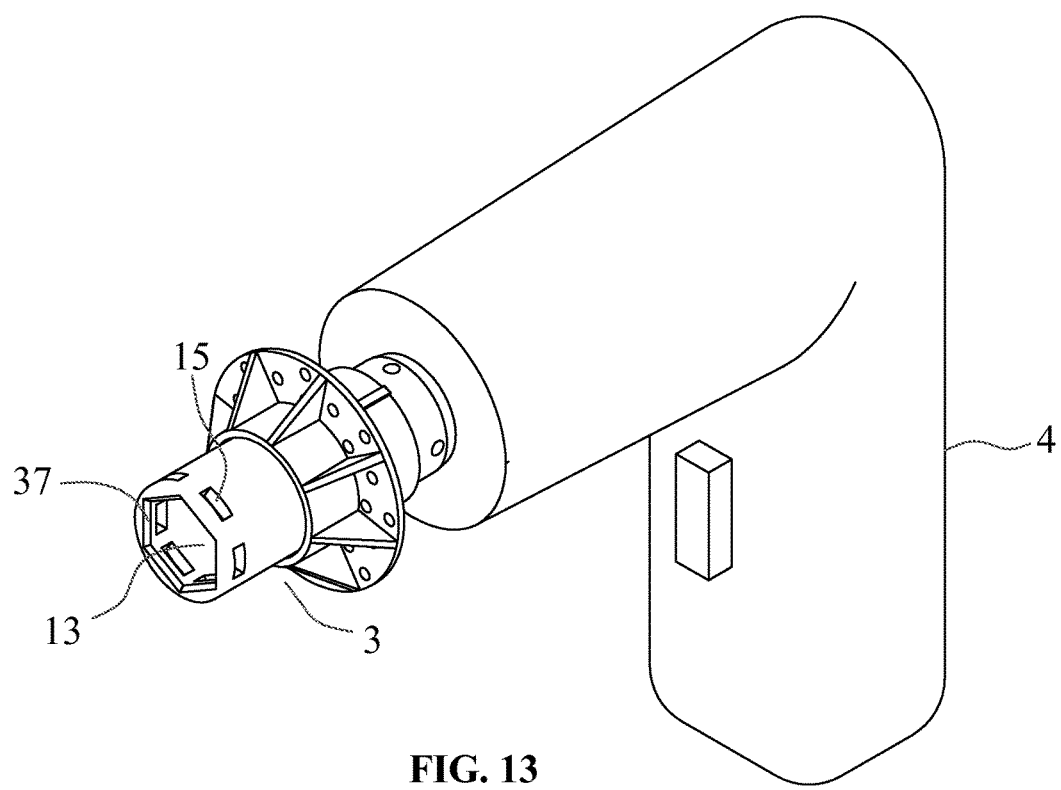
FIG. 13 shows a perspective view of a drill for receiving the assembly formed by the sleeve and the mandrel of the device according to the invention.

The perspective view in FIG. 13 shows a drill 4 on which is mounted the endpiece 3 having a hexagonal cavity 13, for the assembly of the outer sleeve 5 equipped with the mandrel 6, and recesses 15 in which the flexible parts 11 of the connector piece 7 latch.

Referring to FIGS. 2, 3, 12 and 13, the chamfer 35 of the connector piece 7 of the outer sleeve 5 cooperates with the chamfers 36 of the handle 2 and the chamfers 37 of the endpiece 3 of the drill 4 in such a way as to reduce play during the drilling of the bone.

The invention claimed is:

1. A perforating trocar, comprising:
   an outer sleeve having a rigid tube; and
   a mandrel having a rod, the rod being suitable for sliding in the outer sleeve, wherein the rod has a longitudinal groove formed in and along an exterior surface of the rod, the groove in the exterior surface of the rod extending from a distal end to a proximal end of the rod, wherein the mandrel further comprises a stopper at the proximal end of the rod, wherein the groove extends to the stopper, and wherein the stopper comprises a bore extending therethrough,
   wherein the distal end of the rod comprises a perforating tip, wherein the groove extends to a distal end of the perforating tip, the perforating tip formed by bevels at the distal end of the rod, the distal end of the rod comprising first and second cutting ridges extending from the perforating tip to first and second positions, respectively, on an outside diameter of the rod, the second cutting ridge disposed on one face of the groove and being more inclined than the first cutting ridge with respect to the longitudinal axis of the rod.

2. The perforating trocar according to claim 1, wherein the perforating tip is formed by beveled grinding of the distal end of the rod.

3. The perforating trocar according to claim 1, wherein the distal end of the rod comprises three bevels and, wherein the perforating tip is offset from the longitudinal axis of the rod.

4. The perforating trocar according to claim 1, wherein the groove is V-shaped.

5. The perforating trocar according to claim 1, wherein a distal end of the tube comprises at least two segments with a helical cutting edge.

6. The perforating trocar according to claim 1, wherein:
   the outer sleeve additionally comprises a connector piece at a proximal end of the tube, and wherein the stopper is suitable for receiving the connector piece in order to form an integral assembly, and wherein the connector piece is perforated in order to permit the sliding of the rod.

7. The perforating trocar according to claim 6, wherein the integral assembly formed by the outer sleeve and the mandrel is configured to be mounted in a handle or in an automatic rotational drive means.

8. The perforating trocar according to claim 1, wherein the bevels form a pyramidal point.

* * * * *